United States Patent [19]

Stabile

[11] 3,999,068

[45] Dec. 21, 1976

[54] APPARATUS FOR MEASURING THE RADIOACTIVITY OF THE CONTENTS OF TUBE LIKE RECEPTACLES

[75] Inventor: James Stabile, Scarsdale, N.Y.

[73] Assignee: Union Carbide Corporation, New York, N.Y.

[22] Filed: June 16, 1975

[21] Appl. No.: 587,275

[52] U.S. Cl. .............................................. 250/328
[51] Int. Cl.² ........................................... G01T 1/00
[58] Field of Search .................................... 250/328

[56] References Cited

UNITED STATES PATENTS

3,784,826  1/1974  Bagshawe et al. ................. 250/328
3,855,473  12/1974  Burgess et al. ..................... 250/328

Primary Examiner—Davis L. Willis
Attorney, Agent, or Firm—Frederick J. Mc Carthy, Jr.

[57] ABSTRACT

Apparatus for measuring the radioactivity of the contents of a plurality of receptacles supported in a rotatable ring.

2 Claims, 9 Drawing Figures

APPARATUS FOR MEASURING THE RADIOACTIVITY OF THE CONTENTS OF TUBE LIKE RECEPTACLES

The present invention is directed to an apparatus for the measurement of the radioactivity of the contents of a plurality of receptacles supported in a rotatable disc.

In the operation of centrifugal analyzers of the type disclosed in U.S. patent application Ser. No. 468,649, filed May 10, 1974 in the name of S. Shapiro and G. Ertingshausen, radiolabelled liquid is collected in tubes arranged circumferentially in a removeable ring disc. It is important that the radioactivity of the contents of the tubes be measured rapidly, accurately and without undue handling of the tubes.

It is therefore an object of the present invention to provide an apparatus for the rapid and accurate measurement of the radioactivity of a plurality of receptacles arranged in a rotatable disc.

Other objects will be apparent from the following description and claims taken in conjunction with the drawing wherein

FIG. 3 (a) is a diagram related to the rotating mechanism of FIG. 3

Figure 1:
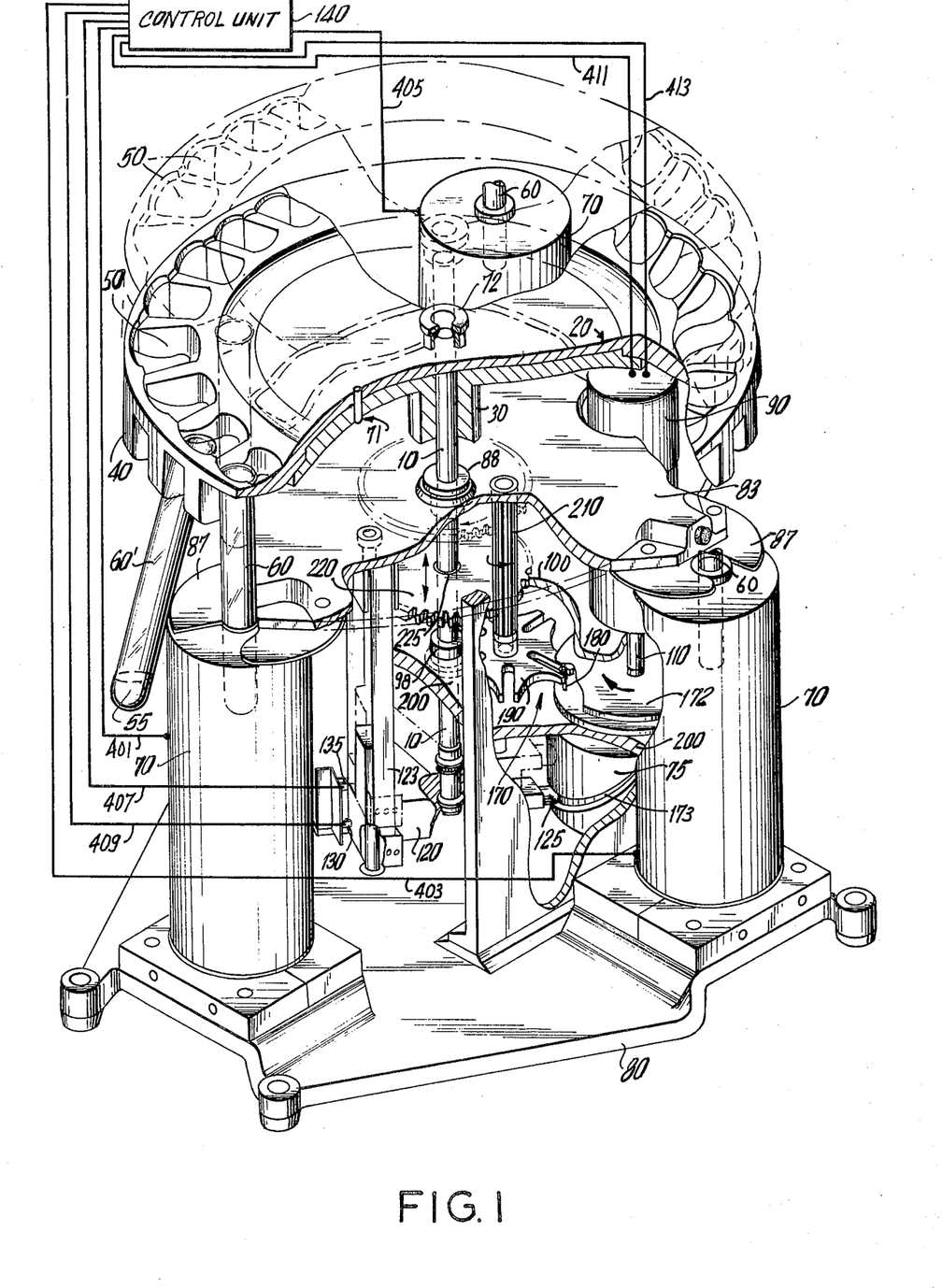
FIG. 1 is an isometric view, partly in section, of the apparatus of the present invention
Figure 1A:
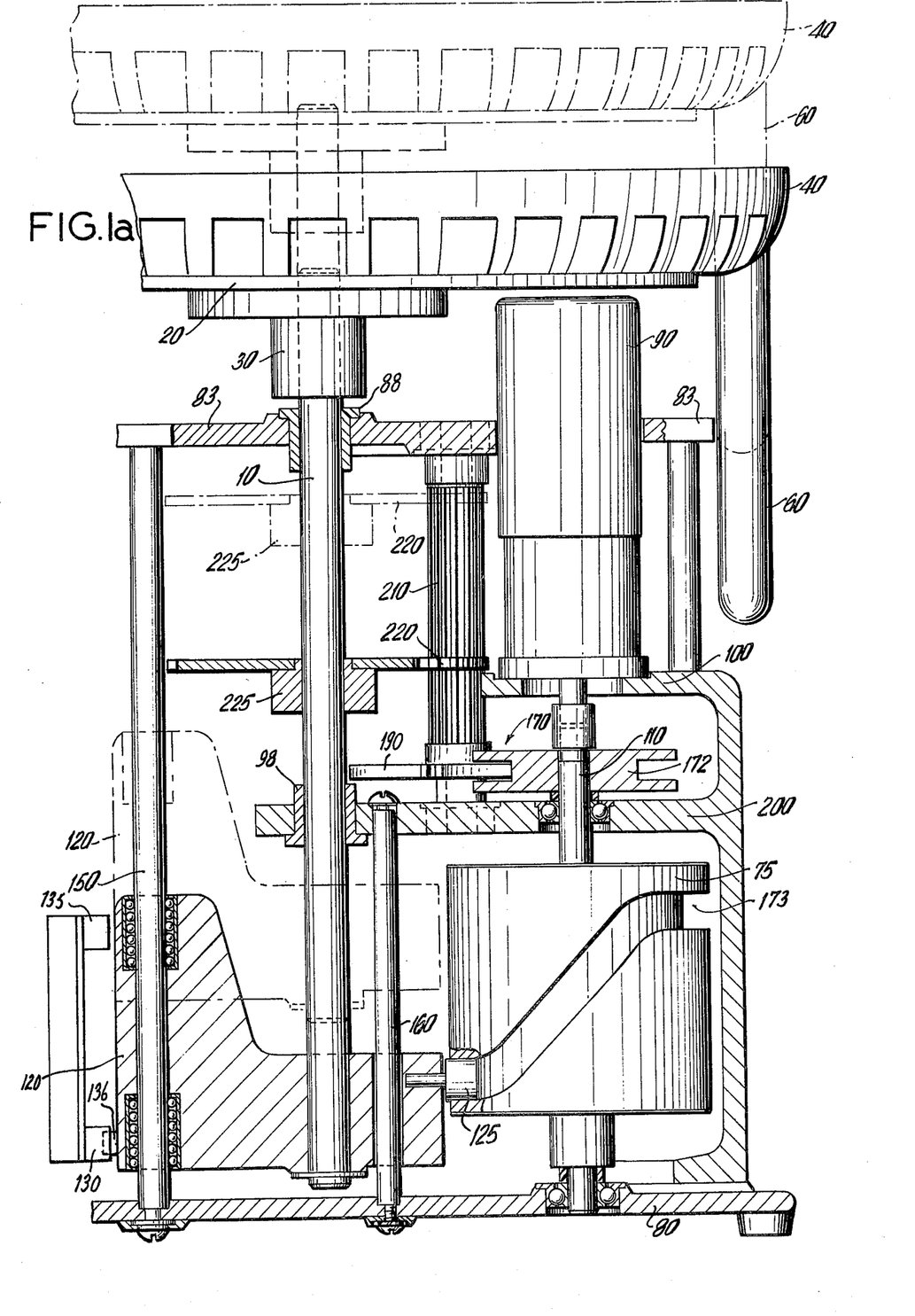
FIG. 1(a) is a sectional elevation view of the apparatus
Figure 1B:
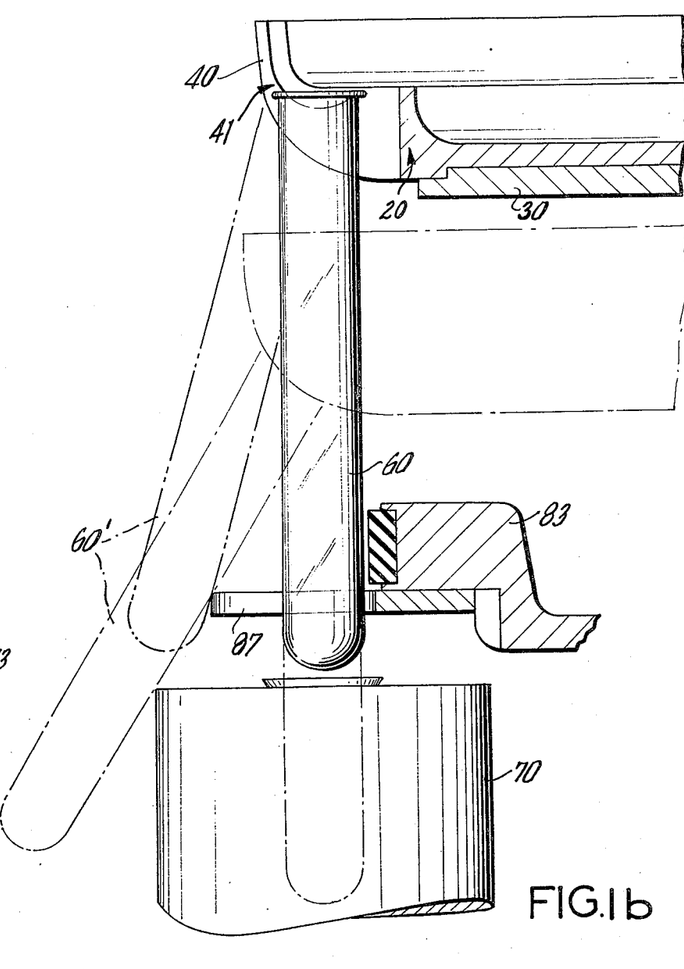
FIG. 1(b) is a partial elevation view of the test tube support arrangement of the apparatus of FIG. 1
Figure 2:
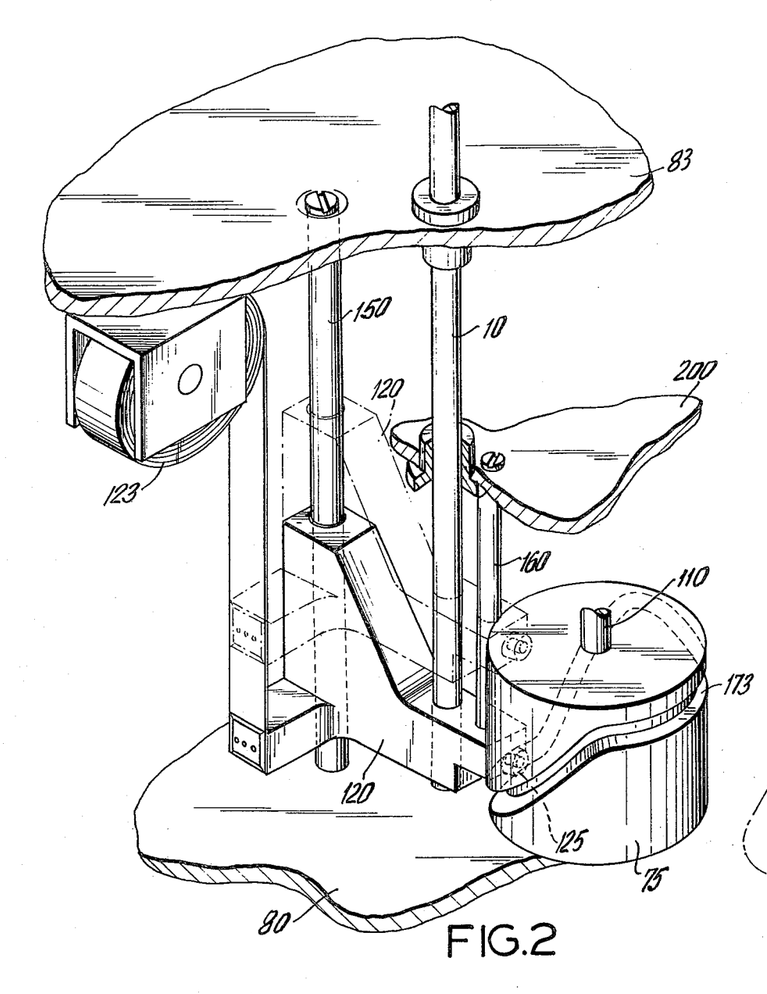
FIG. 2 is an isometric view of the raising and lowering portion of the apparatus of FIG. 1

With reference to the drawing, particularly FIGS. 1 and 1(a) the apparatus of the present invention includes a shaft 10 which is vertically moveable and rotatable about its vertical axis. Shaft 10 extends through two fixed bushing 88 and 98, mounted in plates 83 and 200. A removeable plate member 20 is attached to shaft 10 and is attached to and supported by mounting plate 30. Disc ring portion 40 of plate member 20 having apertures 50, in which are pivotally mounted individual test tubes 60 in the manner indicated at 41 in FIG. 1(b), is affixed to mounting plate by pin arrangement 71. Cap member 72 fits over shaft 10. Disc ring 40 is suitably of the type disclosed in U.S. patent application Ser. No. 468,649 the disclosure of which is incorporated herein by reference. The disc ring 40 has conveniently thirty six equi-spaced supporting apertures 50 which are arranged to permit thirty six test tubes 60 to be supported and pivot and swing outwardly as shown in FIG. 1(b). The test tubes 60 contain a radiolabelled material 55, the radioactivity of which is to be measured by conventional scintillation probes 70, which are mounted on base member 80 at equal intervals of 120° and held in place by plate 83 and deflector extensions 87, as shown in FIG. 1. The initial position of disc ring 40 is the dotted upper position shown in FIGS. 1 and 1(a). In this position a first set of three test tubes 60 is arranged above the three probes 70. Upon actuation of drive motor 90, which is supported on plate 100, and engaged by shaft 110 to cam 75, cam 75 is rotated causing lift block 120, engaged with cam 75 by follower 125, to be lowered to the solid line position shown in FIG. 1 causing the aligned set of three test tubes 60 to be lowered into the underlying three probes 70. In view of the pivotal mounting of the test tubes 60, a test tube 60' adjacent to the tube lowered into probe 70 can swing outward on contact with deflector extension 87. With disc ring 40 in its lowered position, drive motor 90 is deactuated due to the actuation of lower limit switch 130, as hereinafter more fully described, and disc ring 40 remains stationary for a fixed period of time, as hereinafter described, during which period the three probes 70 measure, i.e. count the radioactivity of the test tube which have been lowered therein, and corresponding electrical signals are transmitted to control unit 140 and counted as hereinafter described in connection with FIG. 4. After the predetermined counting period has elapsed, drive motor 90 is reactuated, as hereinafter described, and cam 75 is rotated causing engaged lift block 120 to raise ring disc 40 and test tubes 60 back to the raised position, thus withdrawing the three counted test tubes from the three probes 70. Lift block 120 is held in alignment by guide rods 150 and 160 are a "negator" constant force spring 123 is conventionally connected to lift block 120 and mounted on plate 83 as shown in FIG. 2 to act in the manner of a "counter weight" and relieve the load on drive motor 90 during raising of disc 40. With disc ring returned to its raised position, drive motor 90 remains actuated and the Geneva mechanism indicated at 170 causes shaft 10 and disc ring 40 of plate 20 to rotate an incremental distance to position the next adjacent set of three test tubes 60 over the three probes 70. The Geneva mechanism 170 comprises a driver 172, fixedly coupled to drive motor shaft 110 having a follower 180 which is adapted to engage the driven member 190. Driven member is rotatably supported on support plate 200 and coupled to spline gear 210 which is rotatably engaged between support plates 200 and 83. Upon rotation of the driven member 190, is hereinafter described in conjunction with FIG. 3(a), spline gear 210 rotates, causing the rotation of gear 220 engaged therewith which is fixed to shaft 10 at 225 and moves up and down in engagement with spline gear 210 and rotates shaft 10. The ratio between gear 220 and spline gear 210 is such that mounting plate 20 and disc 40 of plate 20 are rotated, when in their raised position, the incremental amount necessary to bring the next set of three test tubes into position above probes 70. With the next set of test tubes in position, the aforedescribed cycle is repeated, i.e. drive motor 90 rotates cam 75 to cause the lowering of disc 40 and test tubes 60; probes 70 count the radioactivity of the contents of test tubes 60 for a fixed period; test tubes 60 are raised and disc 40 is incrementally rotated. When disc 40 has completed ⅓ of a revolution, all of test tubes 60 have been counted due to the use of three probes 70 and the measurement has been completed and upon the actuation of upper limit switch 135 at this time drive motor 90 is deenergized. The raising and lowering of ring disc 40 and test tubes 30 is more fully illustrated in connection with FIGS. 3, 3(a) and 2(a).

Figure 2A:
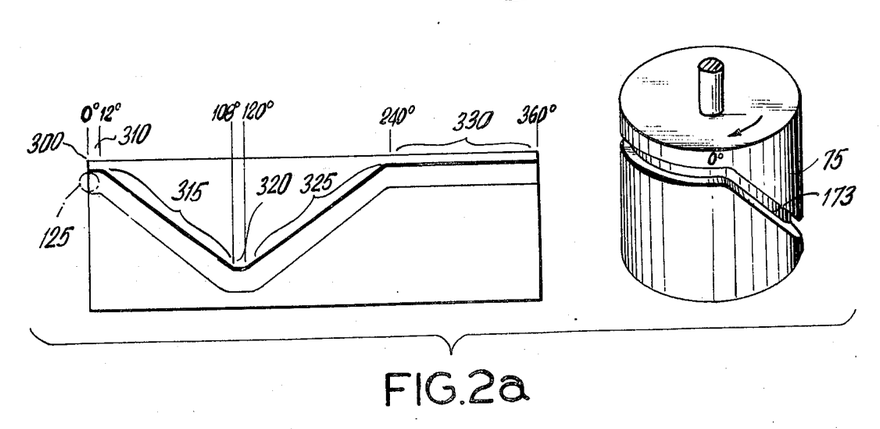
FIG. 2(a) is a cam diagram related to the raising and lowering mechanism of FIG. 2
Figure 3:
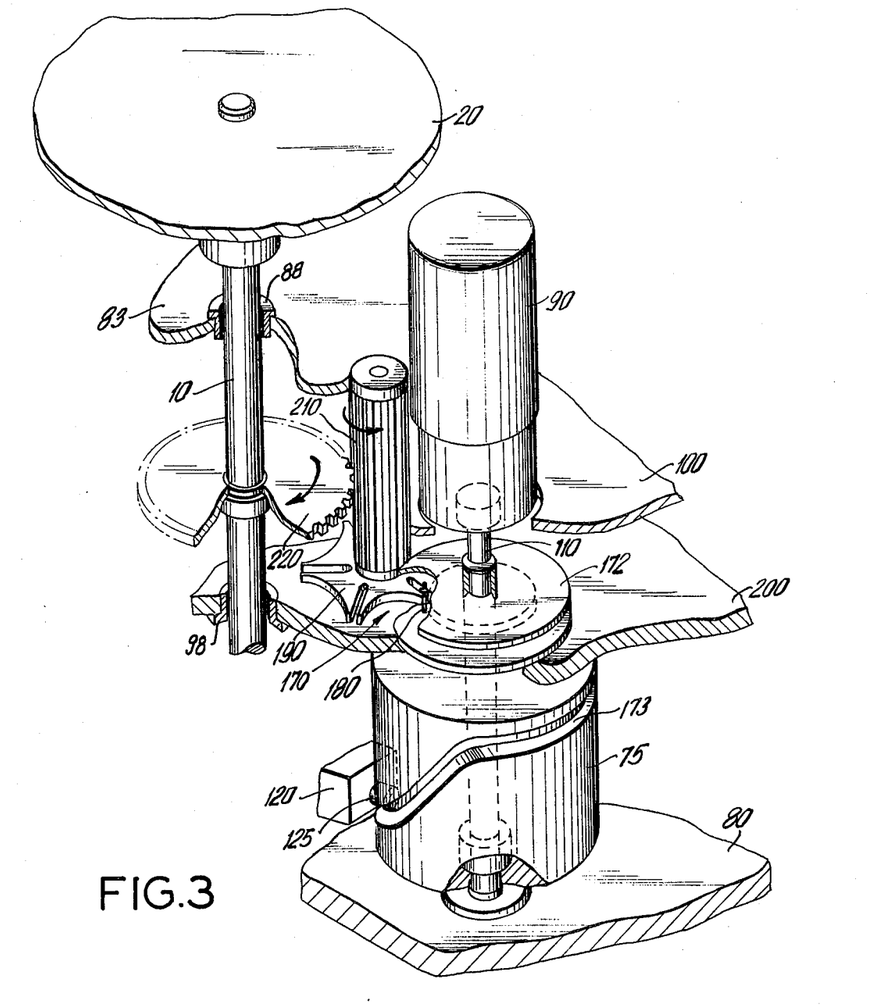
FIG. 3 is an isometric view of the rotating portion of the apparatus of FIG. 1
Figure 3A:
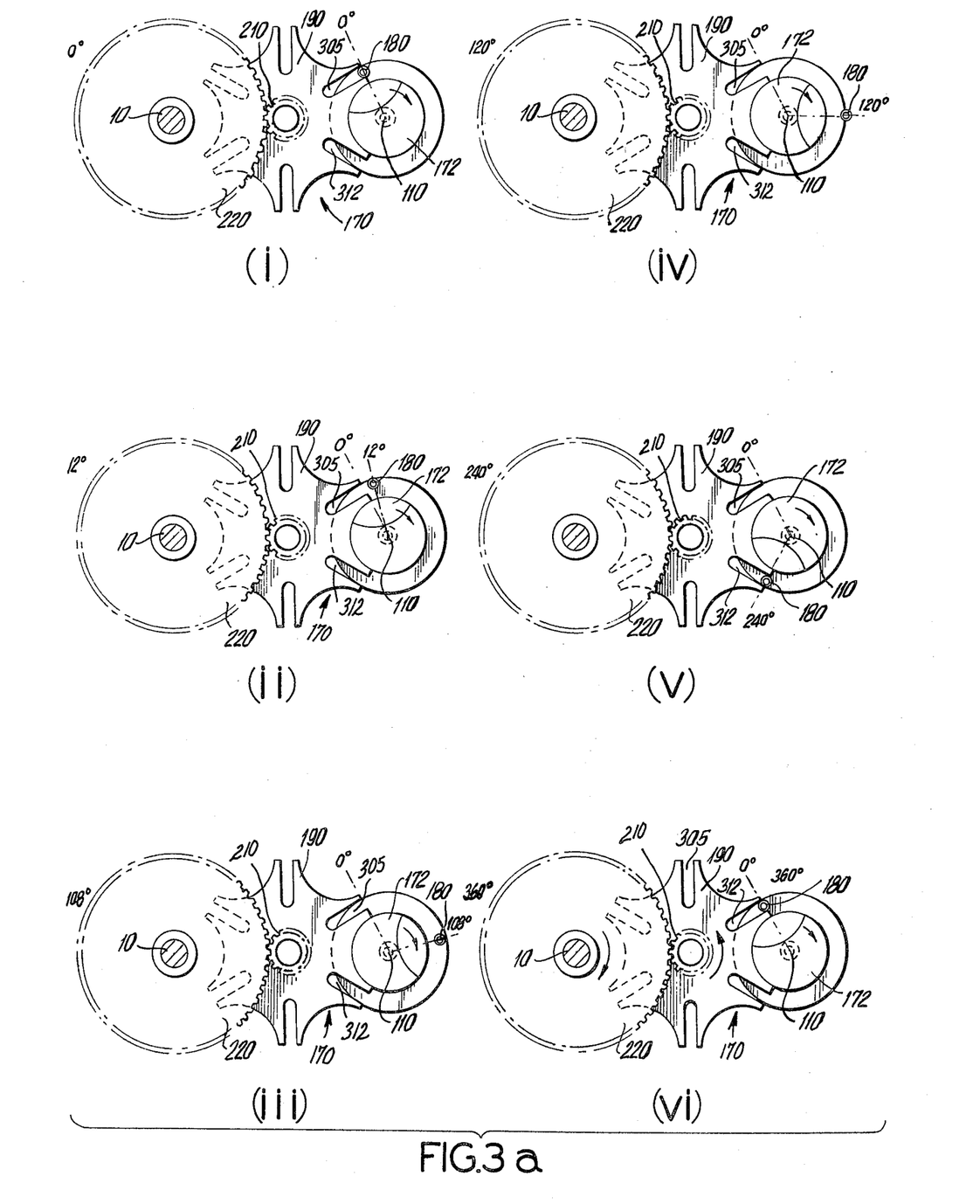

With disc ring 40 of supporting plate 20 in its initial upper position, upon actuation of drive motor 90, motor drive shaft 110 is caused to rotate, causing the rotation of cam 75 and also the driver member 172 of conventional Geneva mechanism 170. The initial position of lift block follower 125, engaged in groove 173 of cam 75 is shown at 300 in the diagram of FIG. 2(a); the initial position of Geneva mechanism 170 is shown in FIG. 3(a) (i) with follower 180 of driver member 172 at the end of slot 305 of driven member 190. As drive motor 90 rotates, follower 125 advances through dwell location 310 and is lowered through location 315, thus lowering block 120 and actuating lower limit switch 130 when the test tubes 60 have been lowered into probes 70. The actuation of lower limit switch 130 deenergizes drive motor 90 for a fixed period of time with follower 125 in dwell location 320; concurrently with the above, driver member 172 of Geneva mechanism 170 has advanced through the position shown in FIGS. 3(a)(ii), (iii) and (iv) which does not result in any movement of driven member 190. The position of FIG. 3(a) (ii) corresponds to the end of the dwell location 310 of cam 75 as shown in FIG. 2(a) and the position of FIG. 3(a) (iii) corresponds to the dwell location 320 of FIG. 2(a)' at which time drive motor 90 is deenergized. After elapse of the predetermined counting period, drive motor 90 is reenergized, causing rotation of cam 75, and Geneva driven member 172, and follower 125 is raised through location 325 of FIG. 2(a) to dwell location 330 in which test tubes 60 have been raised to their initial upper position; concurrently with the above, driver member 172 of Geneva mechanism 170 has been advanced to the position shown in FIG. 3(a) (v) with its follower 180 commencing engagement with slot 312 of driven member 190. Drive motor 90 continues to rotate and advances follower 180 and slot 312 of driven member 190, and hence driven member 190, to the position shown in FIG. 3(a) (vi). The incremental rotation of driven member 190 causes a similar rotation of spline gear 210. Spline gear 210 is engaged to gear 220 on shaft 10 and on account of the selected ratio between gears 210 and 220, advances disc ring 40 of plate 20 an incremental amount which places the next set of three test tubes 60 over probes 70 and drive motor 90 continues to rotate and the foregoing cycle is repeated until all test tubes 60 have been counted and raised to their intial upper position at which time drive motor 90 is deenergized.

The electrical operation of the apparatus of the present invention in the rotating of disc ring 40 of plate 20 to bring succeeding sets of test tubes 30 into position above probes 70 is more fully illustrated in connection with the electrical schematic of FIG. 4.

Figure 4:
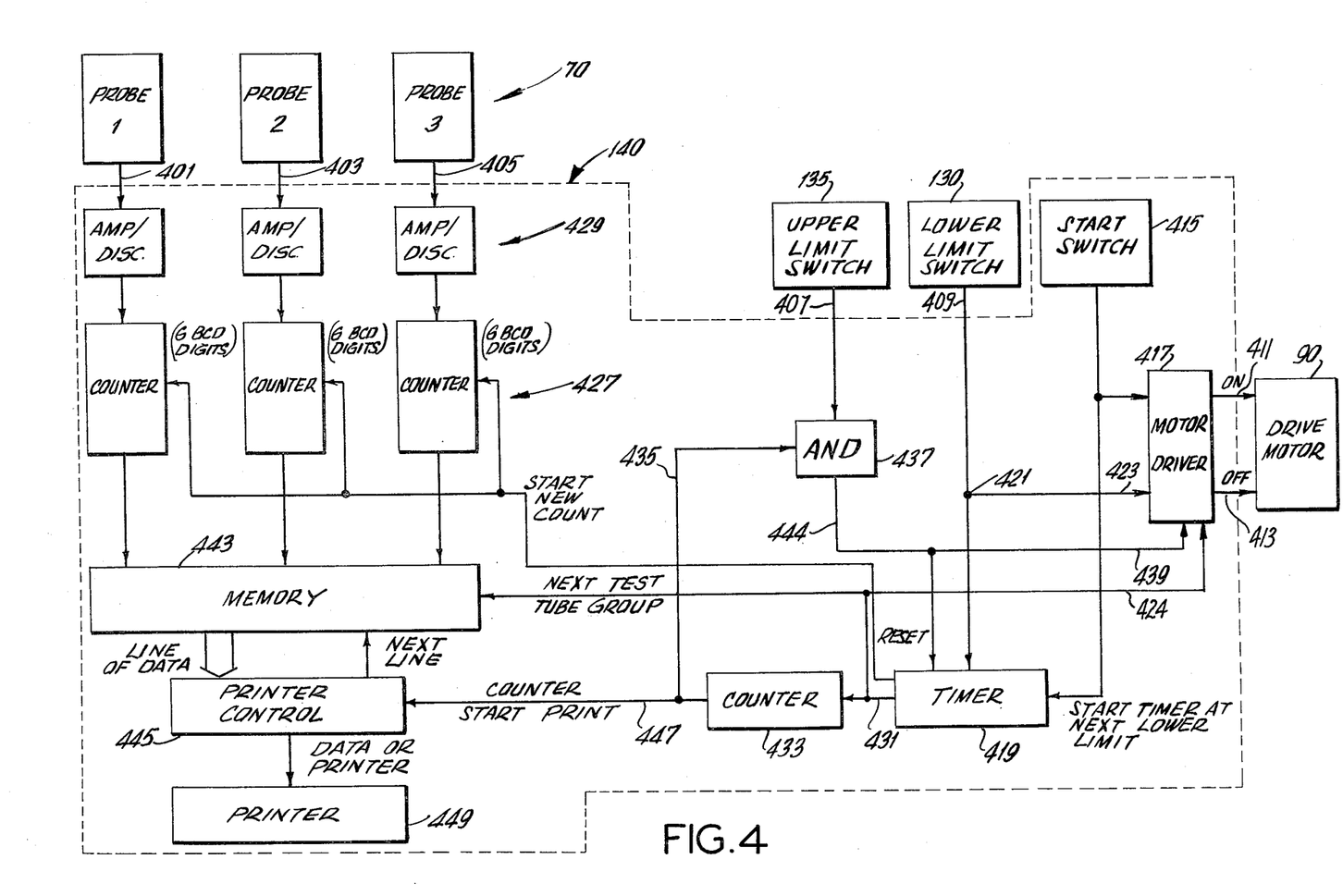
FIG. 4 is a schematic diagram illustrating the electrical operation of the apparatus of FIG. 1
Figure 5:
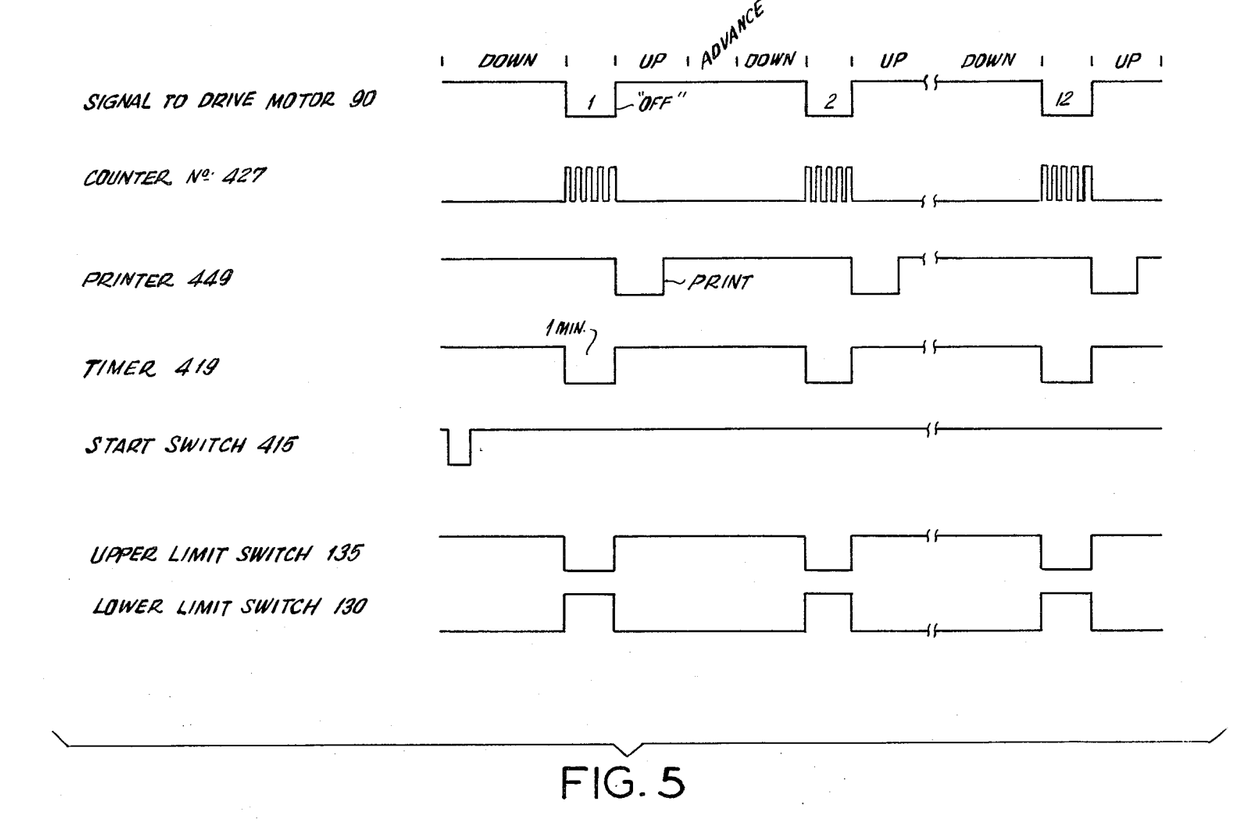
FIG. 5 is a time diagram for the schematic of FIG. 4.

With reference of FIG. 4, the control unit 140 of FIG. 1 is shown within the dotted lines of FIG. 4 comprising conventional components and is connected by leads 401, 403 and 405 to the probes 70 which are each suitably a scintillation counter probe which includes a photomultiplier tube and scintillation crystal which provides a millivolt level output corresponding to the radioactive count of material inserted in the probe.

Upper limit switch 135 and lower limit switch 130, shown in FIG. 1, are suitably electro-optical interrupter type switches, or micro-switches, are connected by leads 407 and 409 to control unit 140, and drive motor 90 receives signals from control unit 140 via leads 411 and 413. In operation, with disc 40 and test tubes 60 in the initial upper position shown in FIG. 1, actuation of start switch 415 provides a signal by way of conventional motor driver unit 417 to cause drive motor 90 to rotate and cause disc 40 and the first set of three test tubes 60 to be lowered to position the test tubes within probes 70. Actuation of start switch 415 additionally provides a signal to timer unit 419 which enables timer unit 419 so that timer unit 419 is actuated by a signal via lead 421 upon the actuation of lower limit switch 130 by tab 121 of lift block 120 when disc 40 reaches its lowered position with the first set of three test tubes 60 within probes 70. Actuation of lower level switch 130 causes drive motor 90 to be deactivated by signal via lead 423 to motor driver 417. Actuation of timer unit 419 provides a signal via lead 425 to BCD counters 427 which causes the counter to commence the accumulation, i.e. count, of the radioactivity of the first set of three test tubes 60 which have been lowered into probe 70 and amplified by conventional amplifier discriminator unit 429.

The deactivation of drive motor 90 by a signal from timer unit 419, is for a predetermined period of time, e.g., one minute, sufficient to obtain adequate radioactive counting for the contents of the test tubes 60 inserted within probes 70.

After the elapse of the predetermined counting periods a further signal from timer unit 419 via lead 424 to motor driven unit 417 reactivates drie motor 90, and disc 40 and the initial set of three test tubes 60 are raised to their initial upper position shown in FIG. 1 and the next set of three test tubes supported on page 40 is advanced to a position in probes 70, in the manner previously described. During the interval when next set of three test tubes 60 is being raised and advanced into position, above probes, a signal from timer unit 419 via lead 441 to memory unit 443 transfers the count information for the first set of three test tubes 60 from counters 427, to memory unit 443. Printer control unit 445 receives a signal via lead 447 after each actuation of timer unit 419 and upon expiration of each counting period and printer 449 prints the count data received from memory unit 443.

Each actuation to timer unit 419 by lower limit switch 130 causes a signal from timer unit 419 to be applied via lead 431 to a counter 433. The output of counter 433 is applied via lead 435 to "AND" gate 437; when the count of counter 433 reaches a number equal to ⅓ of the test tubes, indicating that lower limit switch 130 has been actuated by tab 14 of lift block 120 this number of times. (12 for the 36 test tubes of FIG. 1), the signals provided via lead 440, upon the next actuation of upper limit switch 135 by tab 136 of lift block 120, in conjunction with the output of counter 433 via lead 435, causes a signal is provided from AND gate 437 via lead 444 to Motor Driver 417 to deactivate, i.e. "turn off", drive motor 90.

In the practice of the present invention, the number of tubes supported by ring 40 is suitably from 10 to 50 or more and the number of probes employed is substantially less than the number of tubes to be measured, preferably three; more than three probes can be employed when it is desirable to decrease the over all measuring time.

What is claimed is:
1. Apparatus for measuring the radioactivity of the contents of a plurality of receptacles comprising, in combination,
   a. horizontally disposed support member having a plurality of peripherally arranged apertures for removeably supporting a plurality of downwardly extending elongated receptacles for containing radioactive material
   b. vertically oriented rotatable and reciprocally vertically moveable shaft member engaged to said support member for rotating said support member and for lowering and raising said supporrt member c. a cam member in engagement with said shaft member to cyclically lower and raise said shaft member and said support member a predetermined distance upon rotation of said cam member
d. a plurality of probes for receiving said elongated receptacles supported by said support member and for measuring the radioactivity thereof said probes being arranged below a selected number of said receptacles in alignment with said selected receptacles
e. a geneva drive means in engagement with said shaft member to incrementally rotate said shaft member and said support member an amount which aligns receptacles other than said selected receptacles with said probes
f. drive motor means in engagement with said cam means and said geneva drive means to i. rotate said cam means and cyclically lower said shaft member a predetermined distance and cause said elongated receptacles to be received by said probes and thereafter raise said shaft member to return said elongated receptacles to their initial position
ii. rotate said geneva drive means to incrementally rotate said shaft member and said elongated receptacles upon return to their initial raised position g. electrical switching means arranged to be actuated upon the lowering of said shaft member said predetermined distance to deenergize said drive motor for a predetermined period after said receptacles have been received by said probes.

2. Apparatus in accordane with claim 1 having three equi-spaced probes.

* * * * *